United States Patent [19]

Visca et al.

[11] Patent Number: 4,990,283

[45] Date of Patent: Feb. 5, 1991

[54] MICROEMULSIONS CONTAINING PERFLUOROPOLYETHERS

[75] Inventors: Mario Visca, Alessandria; Alba Chittofrati, Milan, both of Italy

[73] Assignee: Ausimont S.p.A., Milan, Italy

[21] Appl. No.: 259,451

[22] Filed: Oct. 14, 1988

Related U.S. Application Data

[63] Continuation of Ser. No. 41,526, Apr. 23, 1987, abandoned.

[30] Foreign Application Priority Data

Jun. 26, 1986 [IT] Italy .............................. 20910 A/86
Feb. 26, 1987 [IT] Italy .............................. 19494 A/87

[51] Int. Cl.$^5$ .............................................. B01J 13/00
[52] U.S. Cl. ..................................... 252/309; 252/312; 252/49.5; 514/832; 514/833
[58] Field of Search ............ 252/312, 8.554, 309; 514/832, 833; 524/319, 546, 462, 801

[56] References Cited

U.S. PATENT DOCUMENTS

| | | | |
|---|---|---|---|
| 3,778,381 | 12/1973 | Rosano et al. | 514/772 |
| 4,452,818 | 6/1984 | Haidt | 424/352 |
| 4,569,784 | 2/1986 | Moore | 252/312 |
| 4,722,904 | 2/1988 | Feil | 252/312 |
| 4,789,717 | 12/1988 | Giannetti et al. | 526/254 |
| 4,803,067 | 2/1989 | Brunetta et al. | 424/63 |
| 4,859,363 | 8/1989 | Davis et al. | 252/312 |

*Primary Examiner*—Joseph L. Schofer
*Assistant Examiner*—R. H. Delmendo
*Attorney, Agent, or Firm*—Morgan & Finnegan

[57] ABSTRACT

Microemulsions based on perfluoropolyethers, comprising:
 an aqueous medium,
 a perfluoropolyether having a mean molecular weight from 400 to 10,000, and perfluoroalkyl end groups;
 a fluorinated surfactant, and optionally also a short-chain hydrogenated alcohol or a fluoroalkanol, or a water-soluble salt, said microemulsions being permanently stable in a certain temperature range, in which they are preparable by simple mixing of the components.

12 Claims, 3 Drawing Sheets

MICROEMULSIONS CONTAINING PERFLUOROPOLYETHERS

This application is a continuation of application Ser. No. 041,526 filed Apr. 23, 1987 now abandoned.

DETAILED DESCRIPTION OF THE INVENTION

Figure 2:
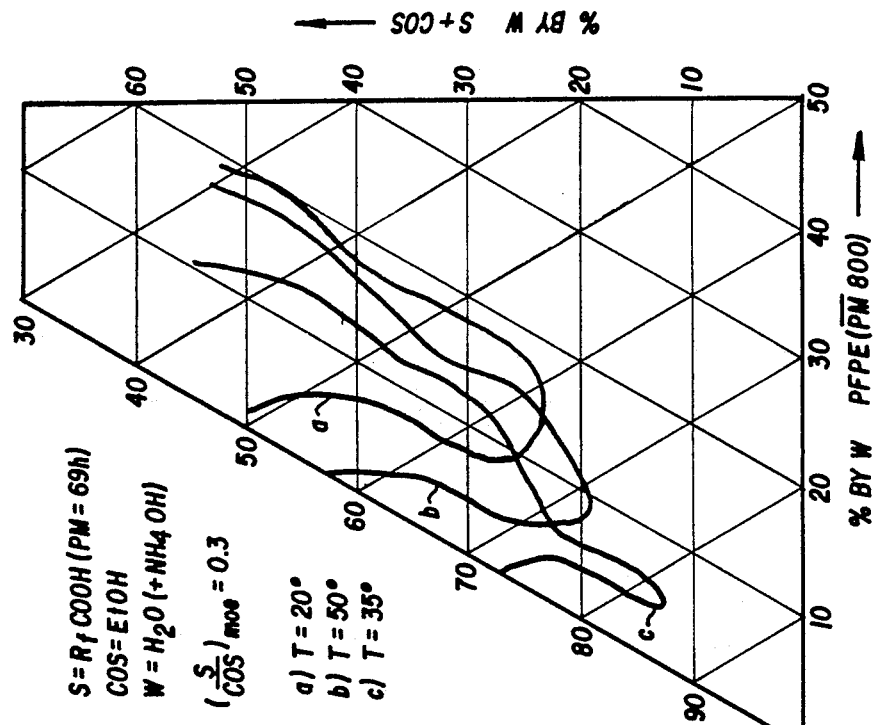

The present invention relates to perfluoropolyether-based microemulsions, which are permanently stable in a certain temperature range and substantially consist of a homogenous limpid or opalescent liquid comprising:
- an aqueous liquid
- a perfluoropolyether
- a fluorinated surfactant and optionally also a $C_1$–$C_{12}$ alkanol (preferably containing from 1 to 2 carbon atoms) or a fluorinated alcohol preferably having perfluoropolyether structure, or alcohol constituted by a partially or completely fluorinated chain.

Also optional suitable additives are water soluble salts capable of modifying the ionic strength of the aqueous solution.

The term "microemulsion", whenever used in the present description, means liquid substances limpid or slightly opalescent in which a liquid immiscible with the liquid forming the continuous phase is present in the form of microdispersed droplets having dimensions not exceeding 2000 Å or it is solubilized in the surfactant mixtures. A microemulsion structure in which the two immiscible phases are both in the form of a continuous tridimensional film (see "Microemulsion Theory and Practice", Academic Press 1977) is considered as possible.

The microemulsions are believed to be systems which are thermodinamically stable in a determined temperature range and form by mixing of the components with one another, at a temperature within the range of stability, without having to supply the system with a considerable dispersion energy, as happens in the case of the conventional emulsions. The latter, as is known, are kinetically stable systems of the irreversible type, in the sense that, once the separation of the liquid phases has occurred, it is not possible to form again the emulsion by simple mixing.

The microemulsions when are brought out from their temperature range of existence in which the microemulsion exists, they tend to separate two phases: however, when they are brought again within such range, the microemulsion spontaneously forms again by simpl mixing. In practice, the microemulsions according to the present invention are indefinitely stable in their stability range.

This behaviour differentiate the systems of this invention from the conventional emulsions, which are characterized by a kinetic but not thermodynamic stability.

In the case of the conventional emulsions, the use of high dispersion energies is always required in order to obtain the dispersion (for example Ultraturrax, ultrasounds, fast dispersing means).

There are known aqueous emulsions of perfluorinated compounds of specific type: for example U.S. Pat. No. 3,778,381 describes microemulsions of fluorinated compounds containing one or two perfluoroisopropoxy groups, said microemulsions being obtained with the support of a fluorohalocarbide containing 1 to 4 carbon atoms, which is evaporated off from the microemulsions at the end of the preparation process. European patent No. 51,526 describes aqueous microemulsions of perfluorohydrocarbons prepared by using non-ionic fluorinated surfactants, which are selected as a function of the temperature range in which the microemulsion has to be stable.

As already mentioned herein, the microemulsions are believed to be characterized by a thermodynamic stability and spontaneously form when the interface tension between the two immiscible liquids falls to values close to zero. Under these conditions, in fact, the microemulsion is obtainable simply by mixing the components and independently of the order of addition of the components.

However, the conditions under which the microemulsions form cannot be foreseen and are strongly depending on the molecular parameters of the liquids and of the surfactants.

In particular, most of the examples reported in literature concern ideal hydrocarbon systems, wherein the hydrocarbon phase consists of a pure compound.

Therefore, these are "monodispersed" systems.

Microemulsions comprising perfluoropolyethers are not known in the technical literature. It is well known that the perfluoropolyethers of commercial type consist of mixtures of products having different molecular weights (polydispersed systems). In the case of the polydispersed systems, the selection of the surfactants is much more complicated because, generally speaking, the type of optimum surfactants to be utilized is different for each individual components, depending on the molecular weight thereof.

Aqeuous perfluoropolyether emulsions are described in Italian patent application No. 20161 A/85 in the name of the Applicant. In this case, however, the emulsion is prepared with the support of an auxiliary oil. Thus, the emulsion in question is a three-phase emulsion: oil/water/perflruoropolyether and, furthermore, it is not thermodynamically stable, the demixing of the emulsion being, in fact, of irreversible nature.

It is apparent how it is advantageous to have available microemulsions instead of emulsions, as the former do not require high dispersion energy for being prepared, are regenerable and indefinitely stable in the time, while the latter must be prepared bearing in mind the order of admixture of the components and providing a high dispersion energy, have a time-limited stability and, when, due to aging, they give rise to a phase separation, in many cases they cannot be restored to the initial state of emulsion even by using the high energy necessary for their generation.

It has now surprisingly been found how it is possible to obtain microemulsions containing perfluoropolyethers, also in the form of mixtures of compounds having the same molecular structure, but a different molecular weight (polydispersed systems) in a wide range of mean molecular weights, in the presence of proper concentrations of fluorinated surfactants and optionally of fluorinated alcohols or of short-chain alkanols. It may be useful also to use, optionally, water-soluble salts, such as $KNO_3$, which have the function of increasing the ionic strength of the aqueous phase and of modifying the interface tension between the immiscible liquids.

Perfluoropolyethers which are suitable for forming the microemulsions object of the present invention are those having a mean molecular weight from 400 to 10,000 and preferably from 500 to 3,000, and belonging to one or more of the following classes:

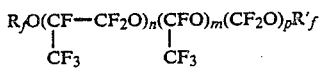 (1)

with a random distribution of the perfluorooxyalkylene units, where $R_f$ and $R'_f$, like or different from each other, are $-CF_3$, $-C_2F_5$, $-C_3F_7$, and m, n, p have such values as to fulfil the abovesaid mean molecular weight conditions;

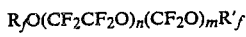 (2)

with a random distribution of the perfluorooxyalkylene units, where $R_f$ and $R'_f$, like or different from each other, are $-CF_3$ or $-C_2F_5$, and m and n have such values as to fulfill the abovesaid conditions;

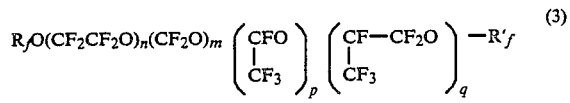 (3)

with a random distribution of the perfluorooxyalkylene units, where $R_f$ and $R'_f$, like or different from each other, are $-CF_3$, $-C_2F_5$ or $-C_3F_7$, and m, n, p, q have such values as to fulfil the abovesaid conditions;

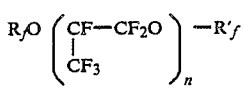 (4)

where $R_f$ or $R'_f$, like or different from each other, are $-C_2F_5$ or $-C_3F_7$, and n has such a value as to fulfil the abovesaid conditions;

 (5)

where $R_f$ and $R'_f$, like or different from each other, are $-CF_3$, $-C_2F_5$, and n has such a value as to fulfil the abovesaid conditions;

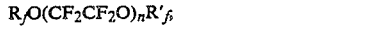 (6)

where $R_f$ and $R'_f$, like or different from each other, are $-CF_3$ or $-C_2F_5$ or $-C_3F_7$, n having such a value as to fulfil the abovesaid conditions.

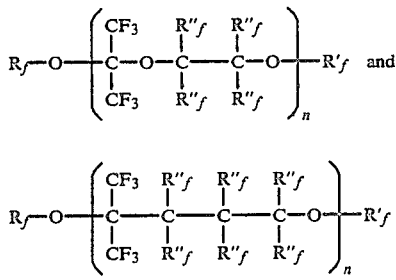 (7)

wherein $R_f$, $R'_f$ are perfluoroalkyl, $R''_f$ are F or perfluoroalkyl, n having such a value as to fulfil the abovesaid average molecular weight range.

Perfluoropolyethers of class (1) are known in commerce under the trademark Fomblin ® Y or Galden ®, the ones of class (2) under the trademark Fomblin ® Z, all of them being produced by Montedison.

Commercially known products of class (4) are the Kryton ® (Du Pont). Those of class (5) are described in U.S. Pat. No. 4,523,039 or in J. Am. Chem. Soc. 1985, 107, 1197–1201.

The ones of class (6) are described in European patent No. 148,482 in the name of Daikin.

The perfluoropolyethers of class (3) are prepared according to U.S. Pat. No. 3,665,041.

The perfluoropolyethers of class (7) are prepared according to the patent application PCT Ser. No. WO87/00538.

The fluorinated surfactants composing the microemulsions forming the object of the present invention can be either ionic or non-ionic. In particular there can be cited; (a) the perfluorocarboxylic acids containing 5 to 11 carbon atoms, and the salts thereof; (b) the perfluorosulphonic acids containing 5 to 11 carbon atoms, and the salts thereof; (c) the non-ionic surfactants indicated in European patent application No. 051,526;

(d) the mono- and di-carboxylic acids deriving from perfluoropolyethers, and the salts thereof;

(e) the non-ionic surfactants comprising a perfluoropolyethereal chain linked to a polyoxyalkylene chain;

(f) the perfluorinated cationic surfactants or the ones deriving from perfluoropolyethers having 1, 2 or 3 hydrophobe chains.

As nonionic fluorated surface-active agents, which are suitable for the purposes of the invention, one can mention the surface-ative agents of the polyoxyethylene-fluoroalkylether type.

When the microemulsions according to the invention are used for oxygen transport in the organism, it is important to select nonionic, nontoxic, fluorated surface-active agents, which are pharmaceutically compatible and have a stability temperature which is close to the temperatures of the human bodies, that is between approximately 35° and 40° C.

A particularly preferred class of surface-active agents of the polyoxyethylene-fluoro-alkylether is the class of compounds with the general formula:

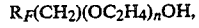

in which $R_F$ is a fluorocarbonated chain or a fluorocarbonated chain which is partially hydrogenated, n is an integer equal to at least 1.

These compounds can be obtained by the method which is the object of French Patent Application No. 80,22,874, filed Oct. 24, 1980 entitled "Method for the Synthesis of Hydrogenated and/or Fluorated Compounds of the Polyoxyethylenealkyl-ether Type, Compounds of this Type, and Application as Nonionic Surface-active Agents". Among these compounds, the compounds with the following formulas are mentioned in particular:

$C_7F_{15}CH_2(OC_2H_4)_4OH$; $C_7F_{15}CH_2(OC_2H_4)_5OH$; $C_7F_{15}CH_2(OC_2H_4)_6OH$;
$C_6F_{13}CH_2(OC_2H_4)_3OH$; $C_6F_{13}CH_2(OC_2H_4)_4OH$; $C_6F_{13}CH_2(OC_2H_4)_5OH$;
and $C_6F_{13}CH_2(OC_2H_4)_6OH$.

The microemulsions of the present invention appear, from a macroscopic standpoint, as one single, clear or opalescent phase, stable within a determined temperature range, depending on structure concentration and average molecular weight of PFPE oil, on the type and concentration of the surfactant, on the possible presence of alcohol and electrolytes, and, in general, on the composition of the aqueous phase.

These microemulsions can be of the type perfluoropolyether (oil phase) in water, wherein the continuous phase is formed by an aqueous liquid (or aqueous solution) and the dispersed phase is formed by perfluoropolyether (PFPE) in form of microdispersed particles having size generally comprised between 50 and 2000 Å, or they are of the type water in PFPE, wherein the dispersed phase is formed by the aqueous liquid (or aqueous solution) in form of microdispersed particles having size generally comprised between 50 and 2000 Å.

Microemulsions of the first type are obtained when the mixture of the three essential component contain aqueous liquid in amount (by volume) higher than that of the PFPE. When the amount of PFPE is prevailing in front of the aqueous liquid it is more probable the formation of microemulsions of the second type.

For both types of microemulsions it results suitable in many cases the addition of a fluorinated or not fluorinated alcohol of the type already mentioned, such additives being defined as co-surfactant.

It is possible in some cases to convert a microemulsion of the first type in a microemulsion of the second type, or vice versa, by adding respectively PFPE or water to the composition and/or by changing the temperature of the composition.

The passage from one type of microemulsion to the other occurs through a transient state wherein it is difficult to state which is the continuous phase and which is the dispersed one.

We have ascertained that the structure and the properties of the microemulsions containing perfluoropolyether are established by several parameters, in particular:

type of surfactant and its chemical and physical characteristics;
molecular weight of the surfactant and possible polydispersion;
molecular weight of the perfluoropolyether oil;
type and concentration of the co-surfactant;
temperature;
concentration of electrolyte.

For instance, we can assume that the formation of microemulsions of the type "water in oil" (w/o) is promoted by surfactants having hydrophobic tail longer than that of the surfactants preferred for the formation of "oil in water" (o/w) microemulsions.

Figure 1:
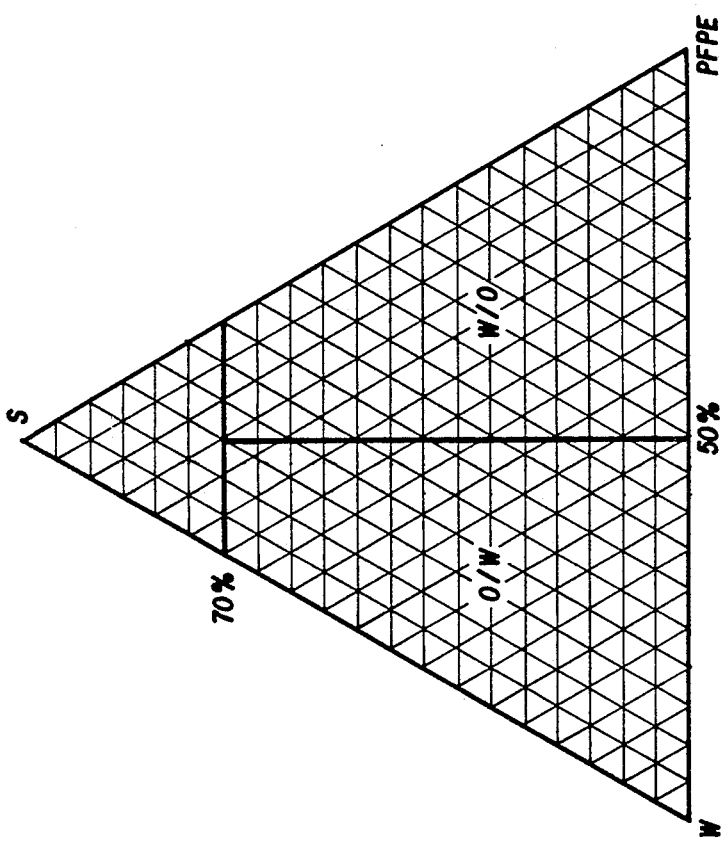

At first we can assume that at constant temperature and ionic force, the continuous phase is the phase prevent in prevailing amount, at least when the content of surfactant and co-surfactant is rather low, preferably lower than 70% by weight as schematically shown in FIG. 1.

In general the microemulsion can be diluted with the liquid of the continuous phase, till remaining in the range of stability. For instance in the case of surfactant consisting of carboxylic acid having perfluoropolyether structure with average equivalent weight 634, in presence of $C_2H_5OH$ as a co-surfactant at a molar ratio surfactant/co-surfactant=0.3, we can obtain microemulsions of perfluoropolyether (PFPE) in water having composition comprised in the existence range shown in FIG. 2 for three different temperatures. These microemulsions are of the type o/w because they are largely diluable with water and contain less than 30% by w. of PFPE oil.

Figure 3:
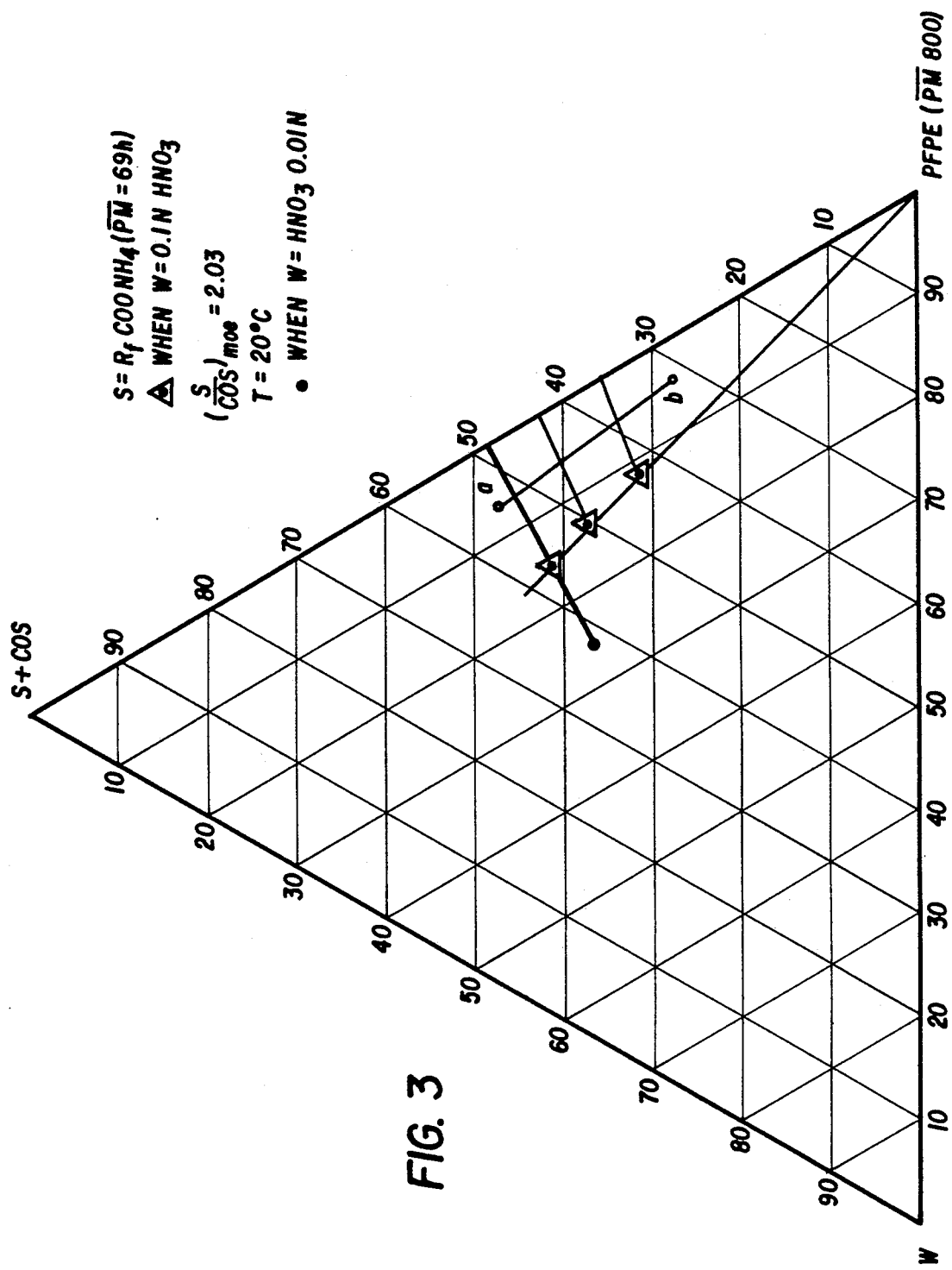

The same surfactant in the presence of the alcohol $H(CF_2)_6CH_2OH$ (as co-surfactant) solubilizes an aqueous solution of $HNO_3 0.1M$ in PFPE oil as shown in FIG. 3, giving a microemulsion of composition: 40% b.w. surfactant+co-surfactant, 15% aqueous phase, 45% PFPE oil. The obtained microemulsion is of the type w/o: indeed it is possible to pass from point a to the point b in FIG. 3 merely adding PFPE oil. We have ascertained that by using more diluted aqueous solution namely 0.01M of $HNO_3$, an higher amount of aqueous phase can be solubilized in the PFPE oil. The assumption that the prevailing phase is the continuous one and that the system can be diluted by this phase, is the basis of an empirical method for the structural analysis of the microemulsions. This method can be applied with the proviso that the content of surfactant is not too high (less than 70% b.w.), because with a high content of surfactant (and optionally also so-surfactant) the microemulsion can be diluted with both phases oil or water, in this case the method is not useful in order to ascertain the continuous phase.

It is also possible a structure of bi-continuous film (see B. W. Ninham, S. J. Chen et al in J. Phys. Chem 90 842-847 (1986) which can occur in anyone position of the phase diagram. In this case, the only method possible for ascertaining the continuous phase is that based on the dilution. In the case when the bi-continuous system contains oil phase and aqueous phase in about the same amount the above method is not easily applicable; but for such systems the distinction between continuous phase and dispersed phase is rather meaningless.

In the case of co-solubilization of the components (dispersion degree at molecular level) it is no longer possible to ascertain the structure of the system (dispersed phase or bi-continuous film), but for such system it is also meaningless to distinguish between w/o or o/w systems.

Figure 4:
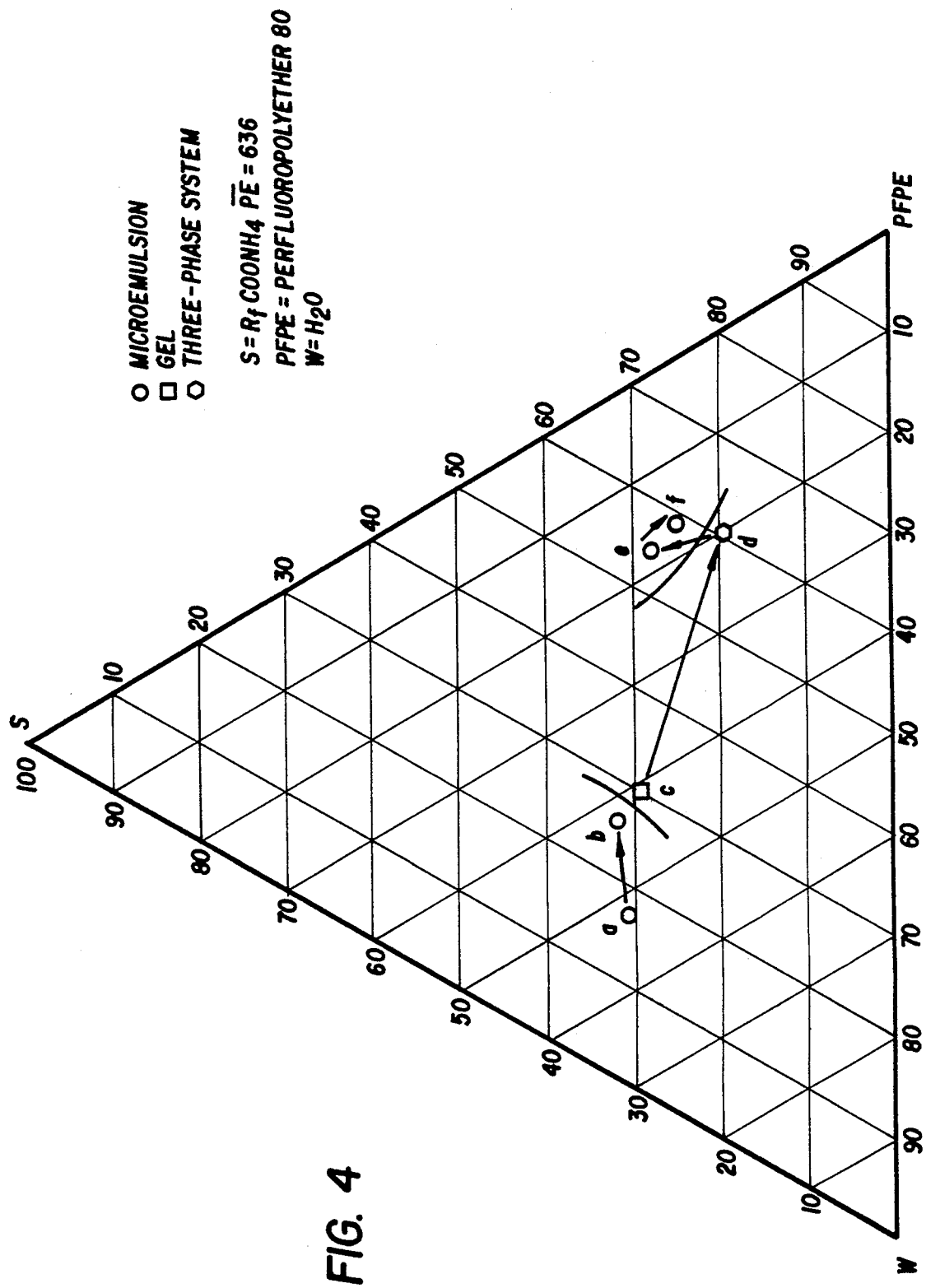

We have also remarked the phase inversion in the case of microemulsions o/w, due to the addition of PFPE oil. This inversion process is shown in the following scheme with reference to the compositions diagram of FIG. 4.

Abbreviations: S=surfactant (ammonium salt of monocarboxylic acid having perfluoropolyether structure of class 1 of average molecular weight 636).

PFPE 800: =perfluoropolyether of class 1, average molecular weight 800. Composition a (microemulsion type o/w, stability range 60°-76° C.)
S=30.5% b.w.
$H_2O$=50.9%
PFPE 800=18.6% b.w.

Through addition of PFPE 800 and S it is obtained a composition b (microemulsion type o/w stable between 60° and 70° C.) wherein:
S=30.9% b.w.
$H_2O$=42.9%
PFPE 800=26.2%

Through further addition PFPE 800 it is obtained a gel substance transparent at t>58° C., composition c wherein:
S=29.4% b.w.
$H_2O$=40.8%
PFPE 800=29.9%

Through further addition of PFPE 800 and S it is obtained a triphase system (at 95° C.: limpid/white/limpid), composition d wherein:
S=19.6% b.w.
$H_2O$=19.3%

PFPE 800=61.1%

Through further addition of S it is obtained a microemulsion of type w/o stable at t>58° C. of composition e wherein:

S=28% b.w.
H$_2$O=17.3% b.w.
PFPE 800=54.8%

Through further addition of PFPE 800 it is obtained a microemulsion of type w/o stable at t>56° C. of composition f wherein:

S=25.5% b.w.
H$_2$O=15.6%
PFPE 800=59.1%

The passage from a microemulsion o/w to a microemulsion w/o in this case occurs through the formation of an intermediate phase having high viscosity showing the formation of liquid anisotropic crystals (birefractive).

The above considerations and statements are given as informations for people skilled in the art in order to prepare microemulsions containing PFPE, of the type o/w and w/o and are not to be considered as limiting rules.

The microemulsions of the present invention can be used in particular in preparing lubricants containing water-soluble additives, in order to confer high stability of the additive dispersion in the oil.

Like known microemulsions of organic fluorinated compounds having more than 4 carbon atoms such as those described in U.S. Pat. No. 3,778,381, the microemulsions of the present invention have a high capability for absorption of oxygen, resulting in its efficient and economical use as a whole blood substitute in the preservation of animal organs.

The microemulsions of the present invention can be used as additive in the polymerization process of fluorinated monomers described in detail in copending U.S. patent application Ser. No. 07/041,525 filed Apr. 23, 1987 U.S. Pat. No. 4,864,006 having as title: "Process For The Polymerization In Aqueous Dispersion Of Fluorinated Monomers." inventors Enzo Giannetti and Mario Visca and the same assignee and filed concurrently with the present application. The content of the abovesaid application is incorporated herein by reference.

EXAMPLES

The following examples are given merely to illustrate possible embodiments of the invention.

EXAMPLE 1

18 g of an acid having the perfluoropolyethereal structure of class (1) defined hereinbefore, having a monocarboxylic functionality (R'$_f$=CF$_2$COOH) containing only little amounts of bicarboxylic acid (R'$_f$=R$_f$=CF$_2$COOH), consisting of a mixture of components having different molecular weights and with a mean equivalent weight equal to 466, were neutralized with 11 ml of an ammonia solution at 10% by weight of NH$_3$ and were diluted to 50 ml with bidistilled water.

25 ml of the resulting solution were heated in a water bath until removal of the NH$_3$ excess. The residue was diluted to 20 ml with bidistilled water.

To the surfactant solution so obtained there were added, under gentle stirring, 1 ml of an alcohol having the perfluoroethereal structure of class (1) and a mean molecular weight of 600, essentially consisting of monoalcohol (R'$_f$=CH$_2$OH) and containing only low amounts of divalent alcohol (R'$_f$=R$_f$=—CH$_2$OH), and then 3 ml of a perfluoropolyether belonging to class (1) composed of a mixture of components having different molecular weights and a mean molecular weight equal to 600. Obtained was a microemulsion characterized by the following properties. It was a limpid, transparent liquid, stable at room temperature. A visual check of the system carried out 2 months after preparation did not reveal any modification of the abovesaid characteristics. When the product was heated to temperatures higher than 40°-50° C., the perfluoropolyether tended to separate and the product got turbid.

By cooling to room temperature, the system spontaneously regained the property of a time-stable microemulsion.

EXAMPLE 2

18 g of an acid having a perfluoropolyethereal structure with the characteristics specified in example 1 and an equivalent weight of 632 were neutralized with 10 ml of an aqueous solution at 10% of ammonia, and additioned with 20 ml of bidistilled water. To the solution so obtained, heated to a temperature of 70° C., there were added, under gentle stirring, 6 ml of a perfluoropolyether belonging to class (1) and having a mean molecular weight of 800.

The resulting compositions was a perfluoropolyether microemulsion, characterized by a stability range at temperatures from 60° C. to 90° C.

The system, brought to room temperature, demixed into its components water and oil. The perfluoropolyether resolubilized spontaneously by heating to temperatures within the stability range.

EXAMPLE 3

To 0.5 ml of an alcohol having a perfluoropolyethereal structure of class 1 (R$_f$=—CH$_2$OH), with a mean equivalent weight of 600 there were added 4 ml of the alkaline solution of the acid having a perfluoropolyethereal structure of class 1 with a mean equivalent weight of 466, prepared as is described in example 1. 0.5 ml of bidistilled water, 3 ml of a perfluoropolyether belonging to class (1) with a molecular weight of 600 and 0.1 ml of 1M KNO$_3$ were then added.

The composition so prepared was found to be composed only of an opalescent phase in the temperature range of from 15° to 23° C. Outside this temperature range, water and perfluoropolyether demixed PFPE resolubilized spontaneously when the system was brought again to its existence temperature range.

EXAMPLE 4

To 2 ml of the alakline solution of surfactant having a perfluoropolyethereal structure, prepared as is described in example 1, there were added 0.1 ml of an alcohol having a perfluoropolyetereal structure belonging to class 1, with a mean equivalent weight of 600, and 0.2 ml of a neutral perfluoropolyether belonging to class 2, with a mean molecular weight of 700.

The system so obtained was a single limpid and transparent phase, which was stable at room temperature and consisted of the solubilized neutral perfluoropolyether.

EXAMPLE 5

A solution containing 10 ml of an acid having a perfluoropolyethereal structure belonging to class (1) and a mean equivalent weight of 690, 10 ml of NH$_3$ at 10% by weight, 6 ml of absolute ethanol and 20 ml of bidistilled water was prepared. To this solution there were added 6 ml of a perfluoropolyether oil belonging to class 1, having a mean molecular weight of 600. The system consisted of a single limpid phase and was stable at room temperature.

EXAMPLE 6

The system described in example 5 was reproduced by adding the components in the following order: oil, acid, water, ammonia, ethanol.

Also in this case a system was obtained, in which perfluoropolyether was solubilized.

EXAMPLE 7

1.53 g of ammonium salt of a bicarboxylic acid with a mean equivalent weight of 500 (mean molecular weight=1000), having a perfluoropolyethereal structure belonging to class (2), were additioned with 3 ml of bidistilled water and 0.8 ml of absolute ethanol. To the resulting solution there were added 0.3 ml of a perfluoropolyether oil belonging to class (1) and having a mean molecular weight of 600; obtained was a limpid composition, stable at room temperature, in which the oil was solubilized.

EXAMPLE 8

1 ml of the solubilized composition reported in example 2 was brought to a temperature of 70° C. and diluted with 1 ml of bidistilled water. The perfluoropolyether resulted to be still solubilized in the composition and to be stable in a temperature range from 40° to 70° C.

EXAMPLE 9

1 ml of the solubilized system reported in example 2 was brought to a temperature of 70° C. and diluted with 2 ml of bidistilled water. A system still consisting of a solubilized perfluoropolyether, stable in a temperature range from 35° to 68° C. was obtained.

EXAMPLE 10

A solution was prepared as is described in example 5. 4 ml of a perfluoropolyether oil belonging to class (1), having a mean molecular weight of 800, was added under gentle stirring to said solution.

A solution consisting of a single limpid phase, stable at room temperature, was obtained.

EXAMPLE 11

A solution was prepared as is described in example 5. 2 ml of a perfluoropolyether oil belonging to class (1), having a mean molecular weight of 1,500, were added under magnetic stirring to said solution. A solution consisting of a single limpid phase, stable at room temperature, was obtained. Oil solubilization was slow, but it can be accelerated by moderate heating.

EXAMPLE 12

A solution was prepared as is described in example 5. To this solution there were added, under magnetic stirring, 0.5 ml of a perfluoropolyether oil belonging to class (1), having a mean molecular weight of 3,000. A solution consisting of a single phase, limpid at a temperature of 50° C., was obtained. Oil solubilization was slow.

EXAMPLE 13

2 ml of the alkaline solution of surfactant having a perfluoropolyethereal structure, prepared as is described in example 1, were additioned with 0.1 ml of an alcohol having a perfluoropolyethereal structure belonging to class (1) and a mean equivalent weight of 600, and with 0.2 ml of a neutral perfluoropolyether belonging to class (3), having a mean molecular weight of 610. A system composed only of a limpid and transparent phase, stable at room temperature, was obtained.

EXAMPLE 14

To 10 ml of a solution of ammonium perfluorooctanoate at 360 g/l there were added 0.5 ml of an alcohol having a perfluoropolyethereal structure with a mean equivalent weight of 780, 2 ml of a solution of 1M $KNO_3$ and 0.5 ml of a perfluoropolyether oil belonging to class 3, having a mean molecular weight of 610. The system consisted of a single phase which was limpid at temperatures >32° C. The system was still stable at temperatures >85° C.

EXAMPLE 15

1 ml of an acid having perfluoropolyether structure of class 1 ($R'_f$=—$CF_2COOH$) and average equivalent weight 694 is neutralized with 1 ml of aqueous $NH_3$ solution (10% b.w. of $NH_3$) and additioned with 0.5 ml $H_2O$ and 0.25 ml of co-surfactant $H(CF_2)_6CH_2OH$. Then 1.4 ml of PFPE average molecular weight 800 of structure of class 1 are mixed therewith obtaining a microemulsion of the type w/o, stable in the range 20°–85° C., having composition:

Surfactant+co-surfactant=35.6% b.w.

aqueous phase=23.8%

PFPE 800=40.6%

The addition of further 1.2 ml PFPE 800 gives a microemulsion stable in the range 25°–85° C. The obtained microemulsion additioned with 0.5 ml $H_2O$ forms a microemulsion w/o stable in the range 35°–75° C.

EXAMPLE 16

1 ml of a carboxylic acid having perfluoroether structure of class 1 ($R_f$=—COOH), with an average equivalent weight of 570, is salified with 1.1 ml of aqueous solution of $NH_3$ (10% by w. of $NH_3$) and diluted with 3 ml of $H_2O$. As a co-surfactant there is added 0.5 ml of an alcohol derivative of perfluoropolyether of class 1 having average molecular weight of 690 and terminal group $R'_f$=—$CH_2OH$. Then 1 ml of aqueous 1 molar solution of $HNO_3$ is added. In the mixture there are introduced 2 ml of an perfluoropolyether (PFPE) of class 1 selected from those having respectively average molecular weight of 600, 650, 800 and 900. The specific gravity of all perfluoropolyethers used is about 1.8 g/ml. The obtained mixture has in all cases a pH value of about 9. The percentage composition is:

surfactant+co-surfactants=26.0% b.w.

water=39.4% perfluoropolyether=34.6%

The obtained microemulsions have stability range as follows:

| PFPE (average molecular weight) | Stability range °C. |
| --- | --- |
| 600 | 36°–48° |
| 650 | 35°–48° |
| 800 | 30°–43° |
| 900 | 33°–44° |

EXAMPLE 17

To 5 ml of a perfluoropolyether of class (1), having an average molecular weight of 650, there are added, 5.40 g of an acid with perfluoropolyether structure, having a carboxy functional group ($R'_f$=—$CF_2COOH$), containing only a few amount of bicarboxylic acid ($R_f$=$R'_f$=—$CF_2COOH$), with an average equivalent weight of 735, salified by means of 1 ml of an aqueous solution of ammonium hydroxide containing 10% of $NH_3$ by weight. The complete dissolving of the aqueous phase in the oil achieved by heating the sample to 40° C. By cooling to room temperature, the separation occurred into two phases, but by heating the sample back to a temperature higher than 40° C., the microemulsion, containing 6.5% by weight of water, formed again spontaneously.

EXAMPLE 18

To 6.56 of the ammonium salt of a carboxy acid having a perfluoropolyether structure, belonging to class (1), having an average equivalent weight of 700, 5 ml of the same perfluoropolyether as disclosed in Example 17, and 3 ml of water are added, with one single clear phase being obtained, which is stable at temperatures higher than 30° C. Such a microemulsion can be diluted with perfluoropolyether up to 4 times its initial volume, in this case a microemulsion being obtained, which is indefinitely stable at room temperature.

EXAMPLE 19

5 ml of said perfluoropolyether as disclosed in Example 17 dissolves 3 ml of water in the presence of 5.34 g of the ammonium salt of carboxylic surface-active agent having a perfluoropolyether structure, belonging to class (1), having an average equivalent weight of 600. A microemulsion, stable at temperature higher than 11° C., forms spontaneously.

EXAMPLE 20

3.4 ml of a perfluoropolyether having an average molecular weight of 600, belonging to class (1), dissolves 2 ml of water in the presence of 1 ml of a carboxy acid having a perfluoropolyether structure, belonging to class (1), having an average equivalent weight of 694, neutralized with 0.6 ml of an aqueous solution of ammonium hydroxide, containing 20% of $NH_3$ by weight, and of 0.4 ml of tert-butyl alcohol. A clear phase, stable at temperatures lower than 30° C., is obtained.

EXAMPLE 21

5 ml of a perfluoropolyether having an average molecular weight of 800, belonging to class (1), dissolves 1.1 ml of water and solution of ammonium hydroxide containing 10% of $NH_3$ by weight, in the presence of 2 ml of a carboxy acid of perfluoropolyether structure, belonging to class (1), with an average equivalent weight of 630. By simply mixing the components, a clear liquid, stable at room temperature is obtained; by heating to a temperature higher than 35° C., the separation into two phases occurs, and the product becomes cloudy; by cooling to a temperature lower than 35° C., the product turns again into a microemulsion stable over time. This microemulsion, which contains 7.9% of water, can dissolve water up to a content of 11.1% of water, with its existence range being reduced to temperature lower than 28° C. The stability range can be extended by the addition of an alcohol having molecular weight 700, deriving from a perfluoropolyether of class (1): in fact, the addition of 1.3% b.w. of alcohol is enough to have a microemulsion indefinitely stable at temperatures lower than 65° C.

EXAMPLE 22

To 2 ml of a perfluoropolyether belonging to class (1), having molecular weight 800, 1 ml of a surface-active agent of perfluoropolyether structure belonging to class (1) and with molecular weight 690, 1 ml of $NH_3$ at 10% by weight, and 0.1 ml of 1-nonanol are added. One single clear phase, stable at temperatures comprised within the range of from 0° C. to >95° C., is obtained.

By the further addition of 0.1 ml of $H_2O$, the stability range results to be from about 1° C. to about 62° C.

EXAMPLE 23

A matrix composed by 5 ml of a perfluoropolyether having an average molecular weight of 800, 1.5 ml of PFPE- structure carboxy acid with average equivalent weight 636 and 0.5 ml of ammonium hydroxide solution at 10% of $NH_3$ by weight, is clear all through the investigated temperature range (from 15°–20° C. to 90°–95° C.) and contains 4.0% by weight of aqueous phase, and 74.1% by weight of oil phase. This matrix is capable of reversibly dissolving water, with the following behaviour:

| Added $H_2O$ ml | w % by weight | Range of Existence of w/OF Microemulsion |
|---|---|---|
| 0.1 | 4.8 | T ≧ 31° C. |
| 0.2 | 5.6 | T ≧ 45° C. |
| 0.4 | 7.1 | T ≧ 63° C. |

EXAMPLE 24

To the matrix as disclosed in Example 23, 0.2 ml of methyl alcohol is added. The system is liquid and isotropic (w=4.0%) all through the investigated temperature range; it is capable or reversibly microdispersing water, showing the following behaviour:

| Added $H_2O$ ml | w % by weight | Range of Existence of w/OF Microemulsion |
|---|---|---|
| 0.1 | 4.8 | any temperatures |
| 0.2 | 5.5 | T ≦ 73° C. |
| 0.4 | 7.0 | T ≦ 67° C. |
| 0.6 | 8.4 | T ≦ 62° C. |
| 1.0 | 11.1 | 36° ≦ T ≦ 59° C. |
| 1.4 | 13.7 | 32° ≦ T ≦ 70° C. |
| 2.2 | 18.4 | 28° ≦ T ≦ 37° C. |

EXAMPLE 25

To the matrix as disclosed in Example 23, 0.2 ml of ethanol is added, a system being obtained, which is liquid and isotropic all through the investigated temperature range, which microdisperses reversibly water, with the following behaviour:

| Added $H_2O$ ml | w % by weight | Range of Existence of w/OF Microemulsion |
|---|---|---|
| 0.2 | 5.5 | any temperatures |
| 0.6 | 8.4 | any temperatures |
| 1.0 | 11.1 | 23 ≦ T ≦ 85° C. |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

What we claim is:

1. Microemulsions of the type "oil in water" or "water in oil," macroscopically constituted by one single homogeneous limpid or translucent liquid, indefinitely stable within a temperature range determined by that range in which they are prepared by mixing their components, comprising as essential components:
   an aqueous solution,
   a fluorinated surfactant, and
   a perfluoropolyether having a mean molecular weight ranging from 400 to 10,000 represented by a formula selected from the class consisting of the following formulae from (A) through (H):

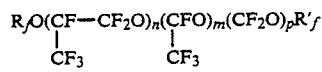   (A)

with a random distribution of the perfluorooxyalkylene units, where $R_f$ and $R'_f$, alike or different from each other, are —$CF_3$, —$C_2F_5$, —$C_3F_7$, and m, n, p have such values as to fulfill the above mean molecular weight condition; (B) $R_fO(CF_2CF_2O)_n(CF_2O)_mR'_f$ with a random distribution of the perfluoroxyalkylene units, where $R_f$ and $R'_f$, alike or different from each other, are —$CF_3$, —$C_2F_5$, and m and n have such values as to fulfill the above mean molecular weight conditions;

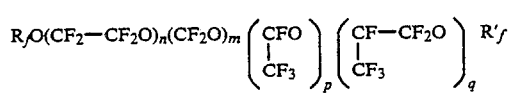   (C)

with a random distribution of the perfluoroxyalkylene units, where $R_f$ and $R'_f$, alike or different from each other, are —$CF_3$, —$C_2F_5$, —$C_3F_7$, and m, n, p, q have such values as to fulfill the above mean molecular weight condition;

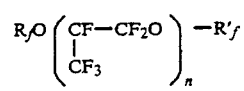   (D)

where $R_f$ and $R'_f$, alike or different from each other, are —$C_2F_5$, —$C_3F_7$, and n has such values as to fulfill the above mean molecular weight condition;

(E) $R_fO(CF_2CF_2O)_nR'_f$, where $R_f$ and $R'_f$, alike or different from each other, are —$CF_3$, —$C_2F_5$, and n has such values as to fulfill the above mean molecular weight condition; (F) $R_fO(CF_2CF_2CF_2O)_nR'_f$, where $R_f$ and $R'_f$, alike or different from each other, are —$CF_3$, —$C_2F_5$, or —$C_3F_7$, and n having such values as to fulfill the above mean molecular weight condition;

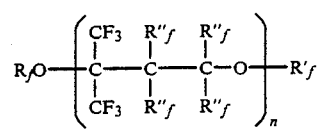   (G)

where $R_f$ and $R'_f$, are perfluoroalkyl, $R''_f$ are F or perfluoroalkyl, n having such values as to fulfill the above average molecular weight range; and

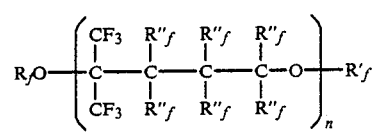   (H)

where $R_f$ and $R'_f$, are perfluoroalkyl, $R''_f$ are F or perfluoroalkyl, n having such values to fulfill the above average molecular weight range.

2. Microemulsions of the type "oil in water" or "water in oil," macroscopically constituted by one single homogeneous limpid or translucent liquid, indefinitely stable within a temperature range determined by that range in which they are prepared by mixing their components, comprising as essential components:
   an aqueous solution,
   a fluorinated surfactant, and
   a perfluoropolyether having a mean molecular weight ranging from 400 to 10,000 represented by the following formula:

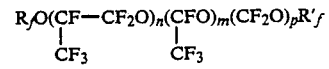

with a random distribution of the perfluorooxyalkylene units, where $R_f$ and $R'_f$, alike or different from each other, are —$CF_3$, —$C_2F_5$, —$C_3F_7$, and m, n, p have such values as to fulfill the above mean molecular weight condition.

3. Microemulsions of the type "oil in water " or "water in oil," macroscopically constituted by one single homogeneous limpid or translucent liquid, indefinitely stable within a temperature range determined by that range in which they are prepared by mixing their components comprising as essential components:
   an aqueous solution,
   a fluorinated surfactant, and
   a perfluoropolyether having a mean molecular weight ranging from 400 to 10,000 represented by the following formula:

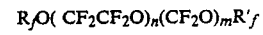

with a random distribution of the perfluoroxyalkylene units, where $R_f$ and $R'_f$, alike or different from each other, are —$CF_3$, —$C_2F_5$, and m and n have such values as to fulfill the above mean molecular weight condition.

4. Microemulsions of the type "oil in water" or "water in oil," macroscopically constituted by one single homogeneous limpid or translucent liquid, indefinitely stable within a temperature range determined by that range in which they are prepared by mixing their components, comprising as essential components:
   an aqueous solution,
   a fluorinated surfactant, a perfluoropolyether having a mean molecular weight ranging from 400 to 10,000 represented by the following formula:

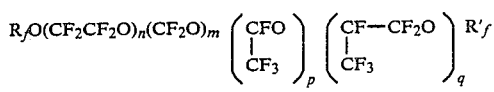

with a random distribution of the perfluoroxyalkylene units, where $R_f$ and $R'_f$, alike or different from each other, are $-CF_3$, $-C_2F_5$, or $-C_3F_7$, and m, n, p, q have such values as to fulfill the above mean molecular weight condition.

5. Microemulsions of the type "oil in water" or "water in oil," macroscopically constituted by one single homogeneous limpid or translucent liquid, indefinitely stable within a temperature range determined by that range in which they are prepared by mixing their components, comprising as essential components:
   an aqueous solution,
   a fluorinated surfactant, and
   a perfluoropolyether having a mean molecular weight ranging from 400 to 10,000 represented by the following formula:

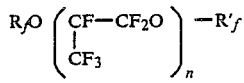

where $R_f$ and $R'_f$, alike or different from each other, are $-C_2F_5$, $-C_3F_7$, and n has such values as to fulfill the above mean molecular weight conditions.

6. Microemulsions of the type "oil in water" or "water in oil," macroscopically constituted by one single homogeneous limpid or translucent liquid, indefinitely stable within a temperature range determined by that range in which they are prepared by mixing their components, comprising as essential components:
   an aqueous solution,
   a fluorinated surfactant, and
   a perfluoropolyether having a mean molecular weight ranging from 400 to 10,000 represented by the following formula:

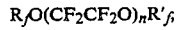

where $R_f$ and $R'_f$, alike or different from each other, are $-CF_3$, $-C_2F_5$, and n has such values as to fulfill the above mean molecular weight condition.

7. Microemulsions of the type "oil in water" or "water in oil," macroscopically constituted by one single homogeneous limpid or translucent liquid, indefinitely stable within a temperature range determined by that range in which they are prepared by mixing their components, comprising as essential components:
   an aqueous solution,
   a fluorinated surfactant, and
   a perfluoropolyether having a mean molecular weight ranging from 400 to 10,000 represented by the following formula:

where $R_f$ and $R'_f$, alike or different from each other, are $-CF_3$, $-C_2F_5$, or $-C_3F_7$, and n having such values as to fulfill the above mean molecular weight condition.

8. Microemulsions of the type "oil in water" or "water in oil," macroscopically constituted by one single honogeneous limpid or translucent liquid, indefinitely stable within a temperature range determined by that range in which they are prepared by mixing their components, comprising as essential components:
   an aqueous solution,
   a fluorinated surfactant, and
   a perfluoropolyether having a mean molecular weight ranging from 400 to 10,000 represented by the following formula:

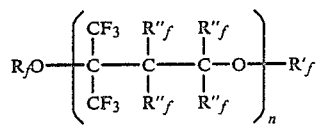

where $R_f$ and $R'_f$, are perfluoroalkyl, $R''_f$ are F or perfluoroalkyl, n having such values as to fulfill the above average molecular weight range.

9. Microemulsions of the type "oil in water" or "water in oil," macroscopically constituted by one single homogeneous limpid or translucent liquid, indefinitely stable within a temperature range determined by that range in which they are prepared by mixing their components, comprising as essential components:
   an aqueous solution,
   a fluorinated surfactant, and
   a perfluoropolyether having a mean molecular weight ranging from 400 to 10,000 represented by the following formula:

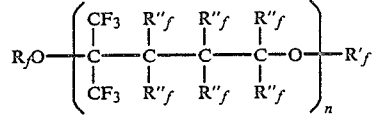

where $R_f$ and $R'_f$, are perfluoroalkyl, $R''_f$ are F or perfluoroalkyl, n having such values as to fulfill the above average molecular weight range.

10. A microemulsion according to any one of claims 1 to 9, characterized further in that is comprises a surfactant the hydrophobic portion of which is a perfluoropolyether chain.

11. A microemulsion according to any one of claims 1 to 9, characterized further in comprising a water-soluble inorganic salt, a fluorinated alcohol or an alkoanol having 1 to 6 carbon atoms.

12. A microemulsion according to claim 2, wherein the perfluoropolyether has a mean molecular weight of about 600 and wherein $R_f = R'_f = CF_3$.

* * * * *